United States Patent [19]

Crainich

[11] Patent Number: 5,312,434
[45] Date of Patent: May 17, 1994

[54] MEDICAL INSTRUMENT

[76] Inventor: Lawrence Crainich, Ceda Industrial Park, Charlestown, N.H. 03603

[21] Appl. No.: 993,630

[22] Filed: Dec. 21, 1992

[51] Int. Cl.⁵ .............................................. A61B 17/42
[52] U.S. Cl. ...................................... 606/207; 606/45; 606/52; 606/170; 606/174
[58] Field of Search ....................... 606/45, 52, 79, 167, 606/170, 171, 174, 207

[56] References Cited

U.S. PATENT DOCUMENTS

| | | | |
|---|---|---|---|
| 2,790,437 | 4/1957 | Moore | 606/170 |
| 3,840,003 | 10/1974 | Komiya | 606/151 |
| 4,512,343 | 4/1985 | Falk et al. | 606/52 |
| 5,009,661 | 4/1991 | Michelson | 606/170 |
| 5,082,000 | 1/1992 | Picha et al. | 606/171 |
| 5,133,735 | 7/1992 | Slater et al. | 606/170 |
| 5,133,736 | 7/1992 | Bales, Jr. et al. | 606/170 |
| 5,141,519 | 8/1992 | Smith et al. | 606/170 |
| 5,147,357 | 9/1992 | Rose et al. | 606/52 |
| 5,156,633 | 10/1992 | Smith | 606/170 |
| 5,171,258 | 12/1992 | Bales et al. | 606/174 |

Primary Examiner—John D. Yasko
Assistant Examiner—N. Kent Gring
Attorney, Agent, or Firm—Bachman & LaPointe

[57] ABSTRACT

A medical instrument includes an elongated tube; a jaw tool, mounted to an end of the elongated tube and having two jaw elements pivotally mounted to each other at a pivot point, each jaw element having an operative end and a linkage end, the operative end and the linkage end extending from the pivot point, the operative end and the linkage end of each jaw element being arranged in a substantially coplaner fashion; an actuating rod for opening and closing the jaw tool, the actuating rod having a thickness and being movably disposed within the elongated tube; a linkage assembly for linking the actuating rod with the jaw tool, comprising two link elements, each link element having a first end pivotally linked to the actuating rod and a second end pivotally linked to the linkage end of a respective jaw element, the first end and the second end of each link element being offset relative to one another so as to compensate for the thickness of the actuating rod and provide proper alignment of each link element between the actuating rod and a respective jaw element; and a handle mounted to the elongated tube and operably connected to the actuating rod so as to actuate the actuating rod whereby the handle can be used to actuate the jaw tool. The second end of each link element preferably interacts with the linkage end of a jaw element so as to provide a closing stop for limiting the extent of closing of the jaw elements.

16 Claims, 6 Drawing Sheets

MEDICAL INSTRUMENT

BACKGROUND OF THE INVENTION

The invention relates to a medical instrument and, more particularly, to medical scissors and/or graspers and the like, the manufacture of which is greatly simplified so as to render the instrument economic to manufacture whether disposable or reusable.

Hand operated medical scissors or graspers are commonly used during various open or laparascopic medical procedures. In order to facilitate such procedures, the tool may be mounted at one end of an elongated tube, with handle means at the other end of the tube, with a mechanical connection disposed therebetween, inside the tube, to operate the tool responsive to manipulation of the handle means.

The instrument and, particularly, the mechanical connection must be sturdy and reliable so as to preclude breakage of the instrument during use and the potentially severe medical consequences stemming therefrom.

Further, the necessity in the medical field for sterility and sharpness makes it desirable for such instruments, or at least the tips or operative portions of such instruments, to be disposable and, therefore, simple and inexpensive in manufacture.

One known approach to the mechanical link is to dispose a push-pull rod, or actuating rod, movably inside the elongated tube. The rod is connected to handle means at one connection between the tool elements and the rod of such known devices is made through straight linkage elements which are connected to the tool elements. The tool elements have laterally offset linkage ends for connection with the straight links. It is costly, however, to manufacture tool elements such as scissor blades or grasper arms, with such a laterally offset section. Thus, such instruments are not sufficiently inexpensive in manufacture and, therefore, may not be readily disposable or economically replaceable.

U.S. Pat. No. 5,147,357 to Rose et. al. is an example of a device having a mechanical connection which uses spherical gears and gear rods to impart the desired motion from a handle structure through an actuating rod to the scissors structure. The spherical gears and gear rods used in Rose et. al. render the instrument expensive in manufacture.

It is preferable, however, as set forth above, for such instruments or the tool elements to be disposable so as to allow the instrument or parts thereof to be discarded after use, thereby avoiding the necessity for sharpening and sterilizing instruments designed for multiple uses.

It is therefore the principal object of the present invention to provide a medical instrument such as medical scissors or graspers which is both reliable and inexpensive in manufacture.

It is a further object of the present invention to provide such an instrument which is small in cross section so as to allow use with an incision of minimal size or through a small sized cannula for laparascopic procedures.

It is still another object of the present invention to provide such an instrument having means for cauterizing the wound formed by the instrument.

Other objects and advantages will appear hereinbelow.

SUMMARY OF THE INVENTION

The foregoing objects and advantages are obtained by the disclosed medical instrument, as follows.

According to the invention, the instrument comprises an elongated tube; jaw means, mounted to an end of the elongated tube and having two jaw elements pivotally mounted to each other at a pivot point, each jaw element having an operative end and a linkage end, the operative end and the linkage end extending from the pivot point, the operative end and the linkage end of each jaw element being arranged in a substantially coplaner fashion; an actuating rod for opening and closing the jaw means, the actuating rod having a thickness and being movably disposed within the elongated tube; linkage means for linking the actuating rod with the jaw means, comprising two link elements, each link element having a first end pivotally linked to the actuating rod and a second end pivotally linked to the linkage end of a respective jaw element, the first end and the second end of each link element being offset relative to one another so as to compensate for the thickness of the actuating rod and provide proper alignment of each link element between the actuating rod and a respective jaw element; and handle means mounted to the elongated tube and operably connected to the actuating rod so as to actuate the actuating rod whereby the handle means can be used to actuate the jaw means.

According to a preferred embodiment of the invention, each jaw element has an inner surface and an outer surface, and inner surfaces of the two jaw elements are adjacent. The second end of each link element is pivotally linked to an inner surface of a respective jaw element and the first end of each link element is offset relative to the second end by a distance substantially equal to about one half of the thickness of the actuating rod.

According to another preferred embodiment of the invention, the jaw means is a scissor means, and the operative end of each jaw element is a scissor blade. Alternatively, the jaw means is a grasper means, and the operative end of each jaw element is a grasper arm which may have a serrated edge.

According to still another preferred embodiment of the invention, an electrode is connected to the elongated tube, and insulating means is disposed around the tube and the electrode so as to electrically insulate an exterior surface of the elongated tube from the electrode while providing electrical communication between the electrode and the jaw means.

BRIEF DESCRIPTION OF THE DRAWINGS

A detailed description of the preferred embodiments of the invention follows, with reference to the attached drawings, in which:

FIG. 1A is a cross section of the actuating rod attachment according to the invention, taken along the lines 1A—1A of FIG. 1;

DETAILED DESCRIPTION

The invention relates to a medical instrument and, more particularly, to an endoscopic scissor or grasper instrument. Such scissor and grasper instruments, as well as any other type of instrument utilizing a similar motion, are referred to herein as jaw instruments.

Figure 1:
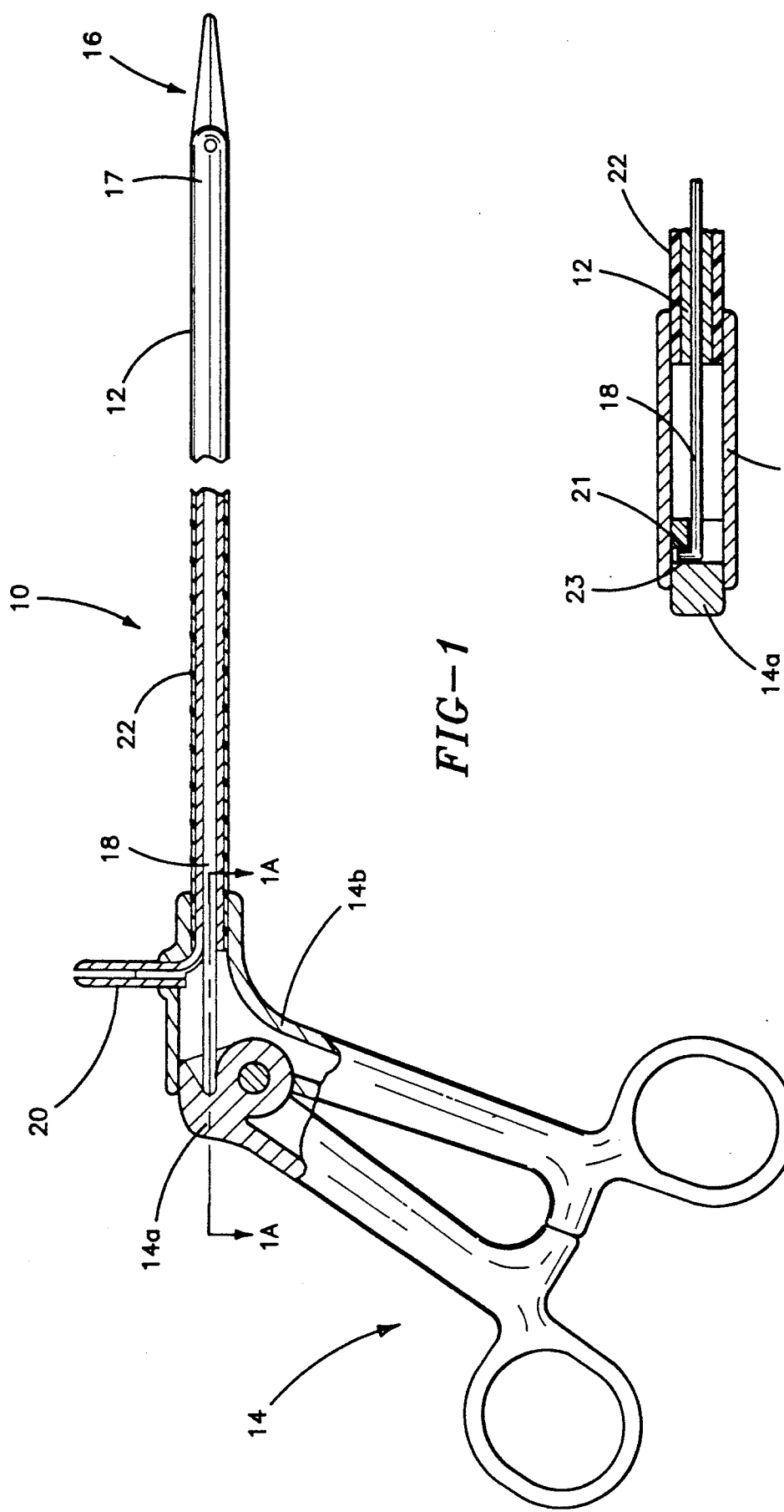
FIG. 1 is a side elevational view of a medical instrument of the present invention.

Referring to FIG. 1, such a jaw instrument 10 is illustrated. Such an instrument typically has an elongated tube 12 having handle means 14 mounted at one end and having the tool 16, such as scissors or graspers, mounted at the other end. Tool 16 may be held to tube 12 through fork means 17. Handle means 14 are typically operative to open and close tool 16 through a connecting or actuating rod 18.

Such an instrument 10 is typically employed during endoscopic or laparascopic procedures to perform functions at inaccessible regions of the body. During such procedures, it is frequently desirable to cauterize the region of the body being worked upon. To this end, an electrode 20 may suitably be disposed on tube 12 and electrically connected thereto. Insulating material 22 may suitably be disposed around tube 12 so as to insulate the outer surface of tube 12 and to insulate handle means 14 from tube 12.

The present invention relates to a linkage structure for operatively linking actuating rod 18 with tool 16.

Figure 2:
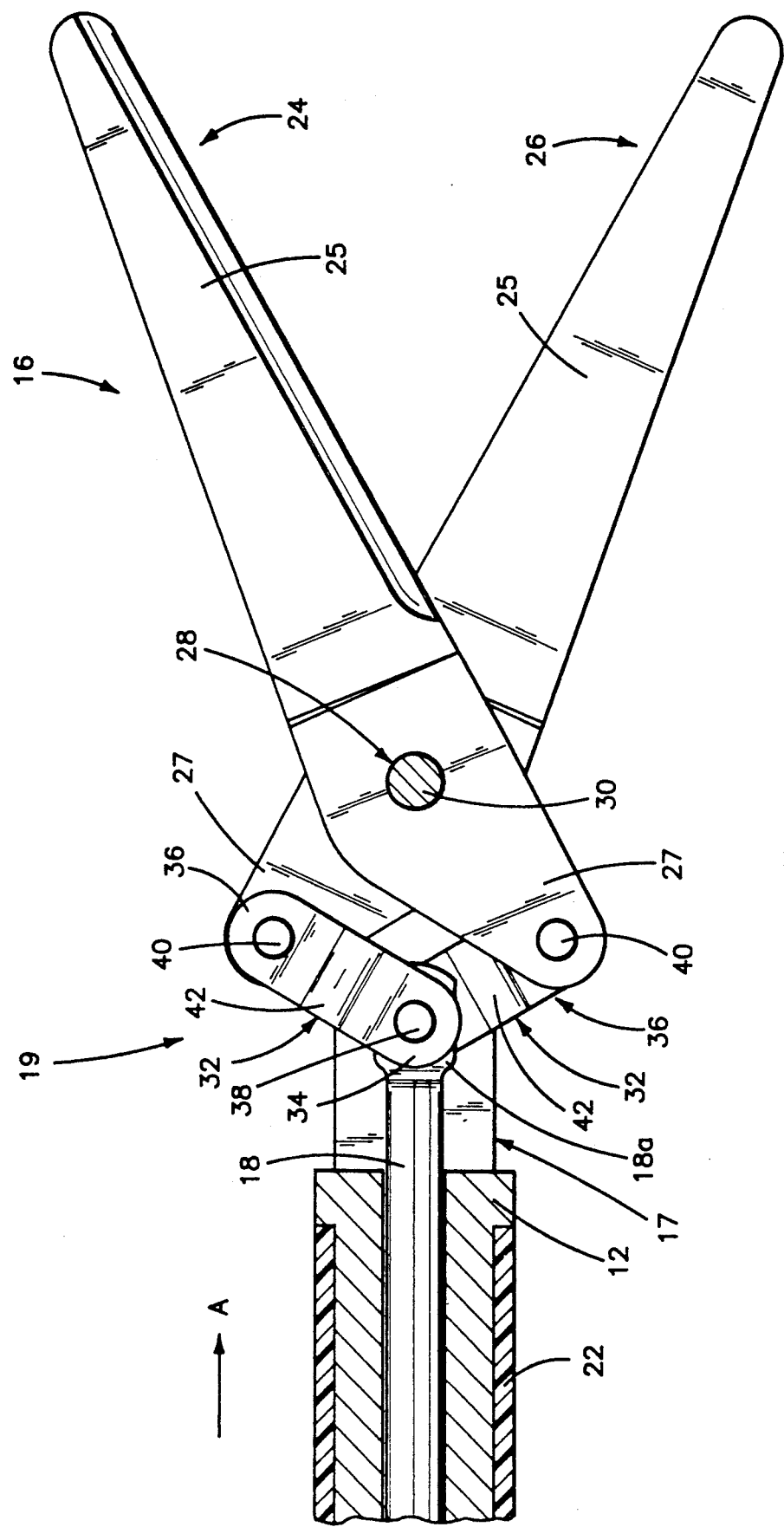
FIG. 2 is a cross section showing a linkage structure for a medical scissors in an open position according to a preferred embodiment of the invention.

Referring now to FIG. 2, the linkage structure of the present invention will be described. FIG. 2 shows tool 16 connected to actuating rod 18 through linkage means 19, the structure of which provides the above described advantages of the present invention. Tool 16 of the embodiment of FIG. 2 is a medical scissor. It should be noted, however, that any type of jaw tool is suitable for use according to the present invention. As used herein, a jaw tool is any tool such as a scissor or grasper or other tool which has two jaw elements which utilize a scissor-like or grasper-like motion.

Figure 4:
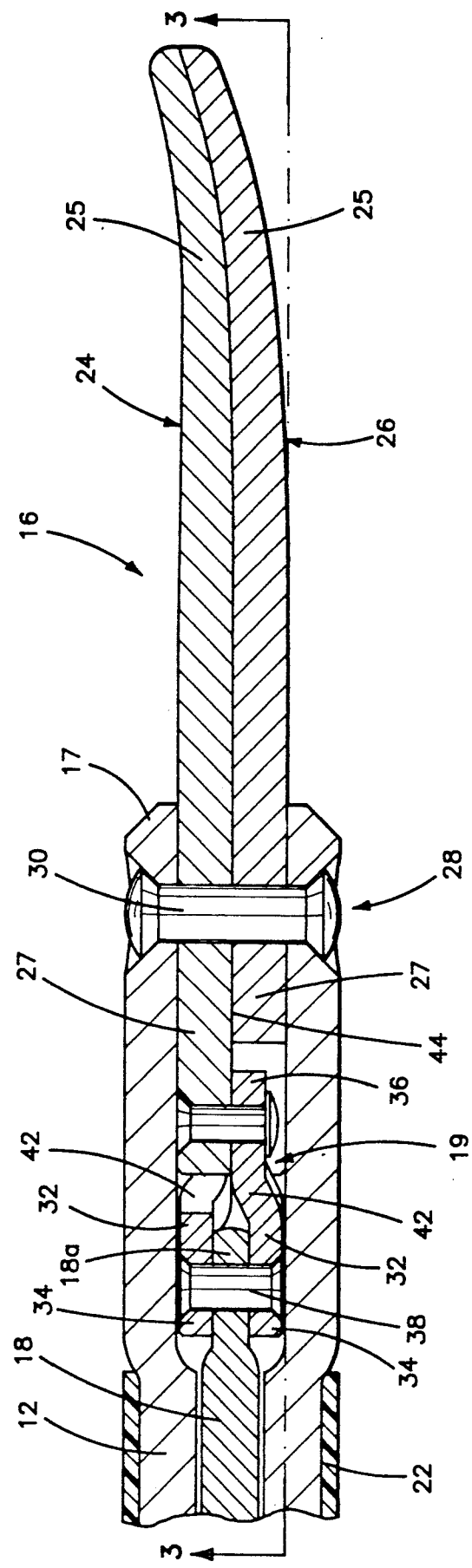
FIG. 4 is a cross section taken along the lines 4—4 of FIG. 3.

As shown in FIG. 2, the jaw tool 16 includes two scissor elements 24, 26 which are pivotally linked to each other at pivot point 28. This link may suitably be made, for example, through a pin 30 or any other means known in the art which provides the desired pivot. Pin 30 is preferably disposed in fork means 17 (as best shown in FIG. 4). Returning to FIG. 2, each scissor element has an operative end 25 and a linkage end 27 extending from pivot point 28. In this embodiment, operative ends 25 are the sharpened scissor blades. Scissor elements 24, 26 are actuated by actuating rod 18 through link elements 32. Each link element 32 is pivotally linked at one end 34 to actuating rod 18 and at the other end 36 to a linkage end 27 of a respective scissor element 24, 26. Link elements 32 are preferably attached to actuating rod 18 at a flattened portion 18a of rod 18. Link elements 32 may be linked to actuating rod 18 through any means known in the art, such as, for example, a pin 38. Preferably, a single pin 38 passes through actuating rod 18 and can be used to mount both link elements 32. Link elements 32 may likewise be linked to scissor elements 24, 26 through any means known in the art, such as pins 40. In this manner, displacement of actuating rod 18 relative to tube 12 will operate scissor elements 24, 26. Displacement of actuating rod 18 in the direction of arrow A will open scissor elements 24, 26 as shown in FIG. 2.

Figure 3:
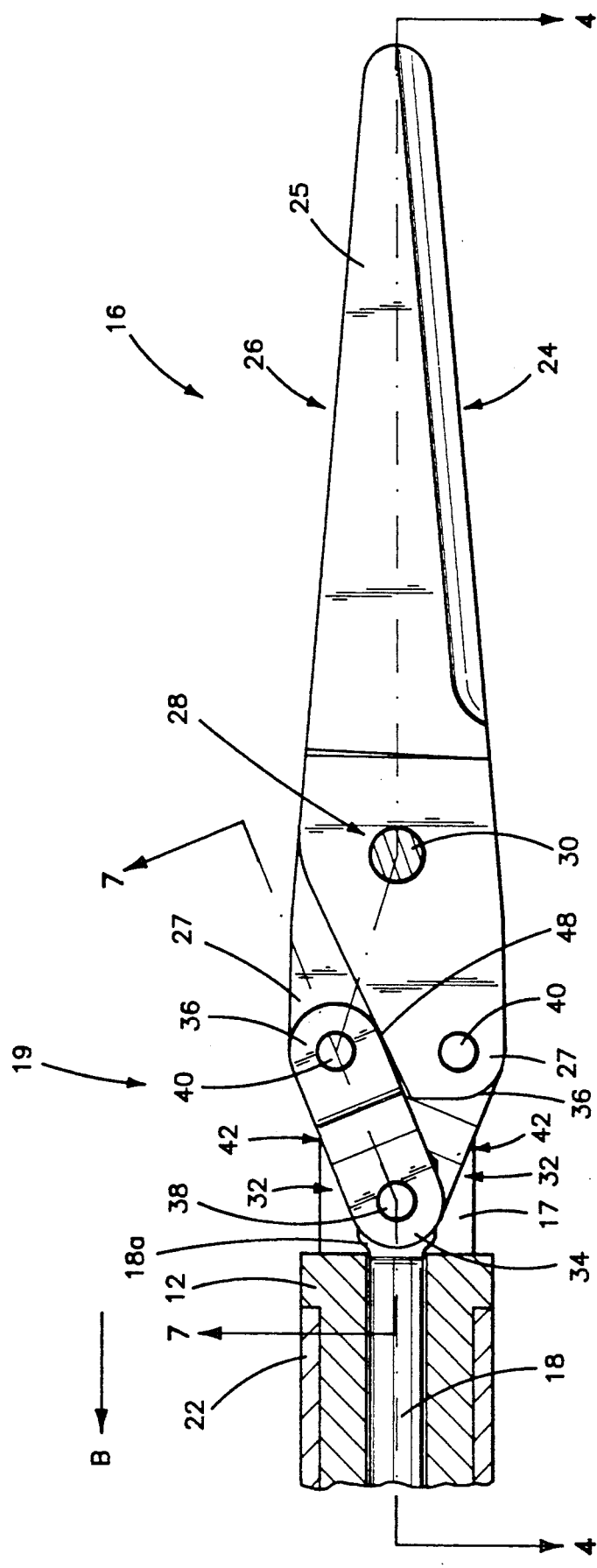
FIG. 3 is a cross section taken along the lines 3—3 of FIG. 4 showing scissors in the closed position.

FIG. 3 shows the embodiment of FIG. 2. with scissor elements 24, 26 closed responsive to displacement of actuating rod 18 in the direction of arrow B.

FIG. 1A shows a cross section of the connection of rod 18 to handle 14. As shown, handle 14 has a moving portion 14a and a stationary portion 14b. Rod 18 is connected to moving portion 14a through any suitable and convenient means. Preferably, rod 18 has an angled end 21 which is disposed in a notch 23 formed in moving portion 14a. Thus, the structure for connection between rod 18 and handle means 14 is simple in manufacture, and is therefore in keeping with the overall objective of the invention to provide an instrument which is economical to manufacture.

FIG. 4 shows a cross section of the embodiment of FIG. 2 and illustrates the structure of the present invention which results in advantageously simple and economic manufacture of the instrument, thus rendering the instrument or instrument tip or tool element thereof suitable for disposal after use.

Scissor elements 24, 26 are shown pivotally mounted in fork means 17 through pin 30. As shown, fork means 17 is preferably formed as an integral portion of elongated tube 12 so as to simplify manufacture of the instrument. Alternatively, fork means 17 or the elements of any tool 16 to be used could be replaceably attached to tube 12 through any conventional connection such as, for example, a thread connection (not shown).

Figure 6:
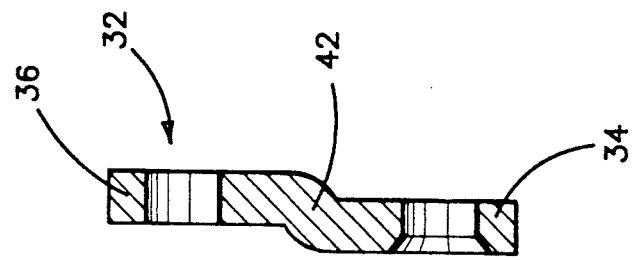
FIG. 6 is a cross section taken along the lines 6—6 of FIG. 3.

According to the invention, link elements 32 are stepped or laterally offset in a manner more fully described below with reference to FIGS. 5-7 so as to allow simplified manufacture of scissor elements 24, 26. In this manner, the operative end 25 and linkage end 27 of each scissor element can be arranged substantially in the same plane. No intricate structure or offset of the scissor elements 24, 26 is necessary. Thus, no additional machining or tooling steps are necessary during the manufacture of scissor elements 24, 26. This greatly reduces the cost of manufacturing the scissor elements, and thereby renders the instrument or tips more disposable due to economics of manufacture.

Figure 5:
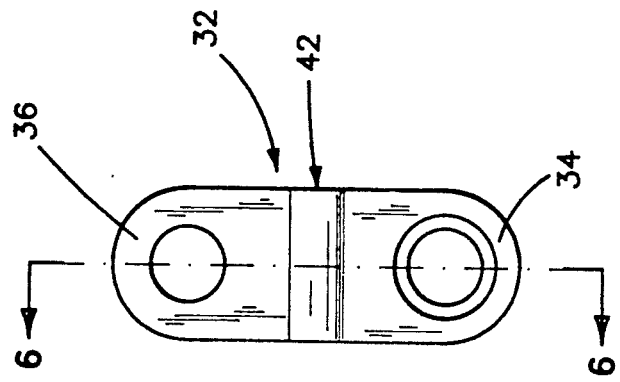
FIG. 5 is a side elevational view of a link element according to the invention.

Referring to FIG. 5, a top view of a link element 32 according to the invention is shown. FIG. 6 is a cross section of FIG. 5 which illustrates the stepped or laterally offset portion 42 of link elements 32. According to the invention, laterally offset portion 42 is laterally offset in an amount sufficient to allow proper alignment of link element 32 between the connection with actuating rod 18 and the connection with a respective scissor element 24, 26.

Figure 7:
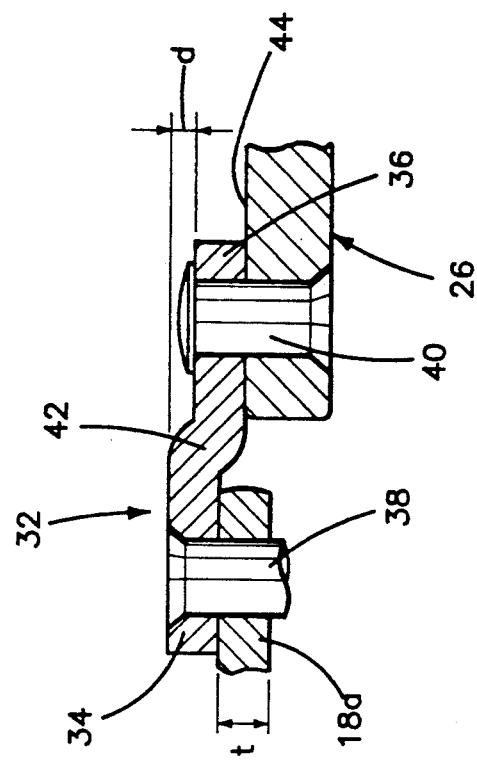
FIG. 7 is a cross section taken along the lines 7—7 of FIG. 3.

FIG. 7 shows a cross-section of a portion of FIG. 3 in order to more fully illustrate the structure and function of link element 32. End 36 of each link element 32 is preferably linked to an inside surface 44 of respective scissor elements 24, 26, while end 34 of each link element is preferably linked to a respective side of actuating rod 18. According to the invention, link elements 32 are laterally offset in order to accommodate the thickness of actuating rod 18, preferably flattened portion 18a of rod 18. In this configuration, according to the invention, the stepped portion 42 of each link element 32 is preferably laterally offset a distance (d) substantially equal to about one half of the thickness (t) of actuating rod 18 or flattened portion 18a thereof. It should be noted that an equal lateral offset of each link element 32 allows a symmetrical configuration of linkage means 19 and, advantageously, allows the manufacture of the instrument according to the invention with a single link element 32 which is suitable for both elements of linkage means 19.

Referring back to FIG. 3, end 36 of each link element 32 may additionally cooperate with linkage end 27 of a scissor element 24, 26 so as to provide a stop means to limit the extent of closing of the scissors. Preferably, end 36 of each link element 32 interacts with linkage end 27 of the scissor element 24, 26 attached to the other link element 32. Closing of the scissors will be stopped upon contact between end 36 and linkage end 27 in the vicinity of, for example, points 48 as shown in FIG. 3.

As previously mentioned, surgical procedures utilizing instruments such as that of the present invention frequently require a cauterization of the operated area after the procedure. Thus, an electrode 20 is preferably provided on the elongated tube 12 so as to provide an electrical connection with the tool 16. Insulating material 22 is disposed around the elongated tube 12 so as to insulate the handle means from the electrode. The overall objective of simplifying the manufacture of the instrument may preferably be served, according to the invention, by forming electrode 20 as an integral portion of elongated tube 12.

Figure 8:
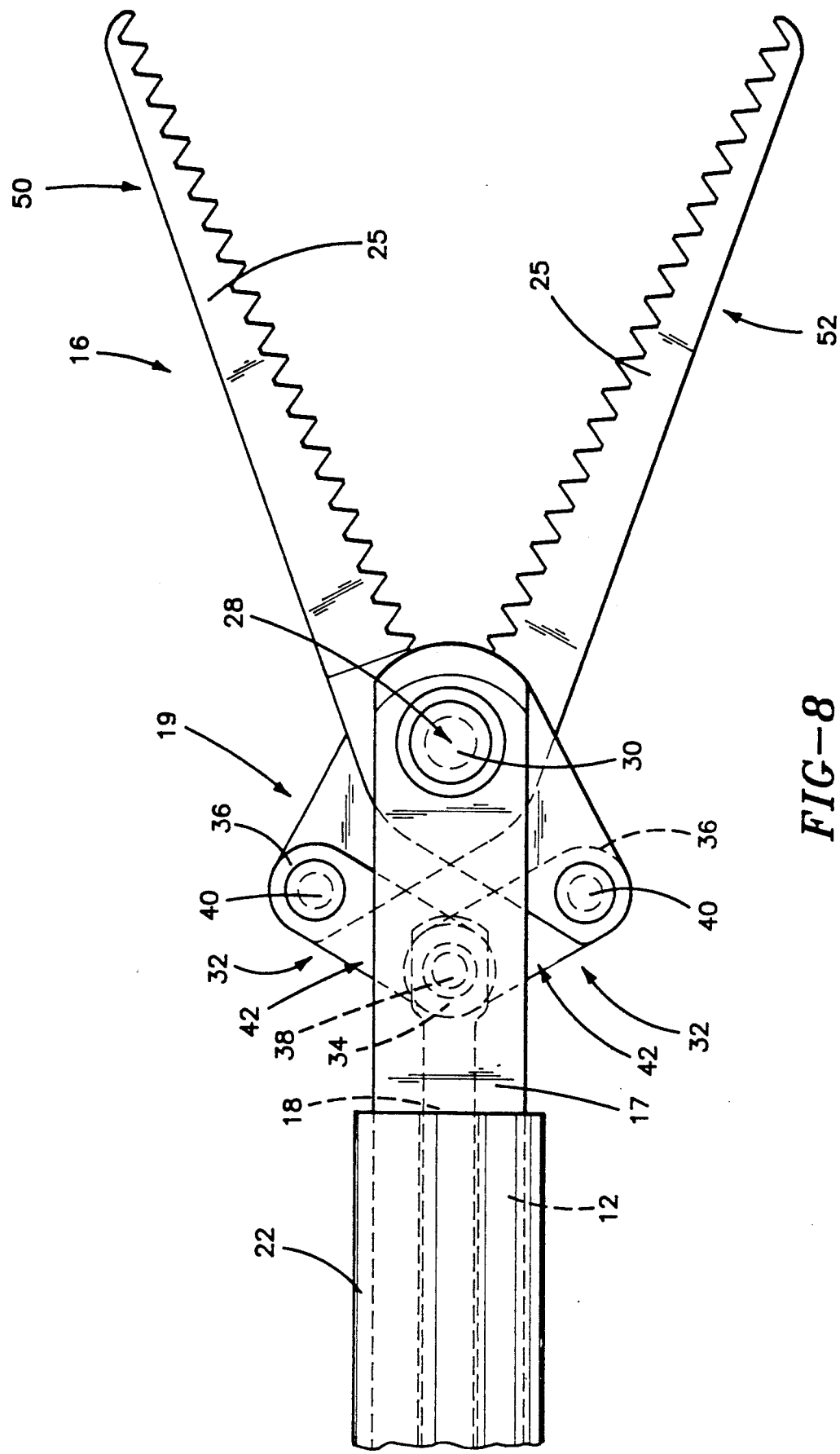
FIG. 8 is a side elevational view of an alternate embodiment of the invention relating to a grasping device.

FIG. 8 shows an alternate embodiment of the invention, wherein the jaw tool 16 is a grasper tool having two grasper elements 50, 52. All other elements are similar to those described in the previous embodiment, and therefore bear the same reference numerals. Any type of tool which has two elements which pivot relative to one another would of course be suitable for use according to the invention. Thus, the present disclosure is not intended to be limited to medical instruments using only scissors or graspers.

It is to be further understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modification which are within its spirit and scope as defined by the claims.

What is claimed is:

1. A medical instrument, comprising:
   an elongated tube having a first end and a second end;
   jaw means, mounted to the first end of the elongated tube and having two jaw elements pivotally mounted to each other at a pivot point, each jaw element having an operative end and a linkage end, the operative end and the linkage end extending from the pivot point, the operative end and the linkage end of each jaw element being arranged in a substantially coplaner fashion;
   an actuating rod for opening and closing the jaw means, the actuating rod having a longitudinal axis and a thickness and being movably disposed within the elongated tube;
   linkage means for linking the actuating rod with the jaw means, comprising two link elements, each link element having a first end defined in a first plane and pivotally linked to the actuating rod and a second end defined in a second plane and pivotally linked to the linkage end of a respective jaw element, the first plane of the first end and the second plane of the second end of each link element being offset relative to one another in a direction substantially perpendicular to the longitudinal axis of the actuating rod so as to compensate for the thickness of the actuating rod and provide proper alignment of each link element between the actuating rod and a respective jaw element; and
   handle means mounted to the second end of the elongated tube and operably connected to the actuating rod so as to actuate the actuating rod whereby the handle means can be used to actuate the jaw means.

2. A medical instrument according to claim 1, wherein the elongated tube includes fork means at the first end, the jaw means being pivotally mounted on a pin disposed within the fork means.

3. A medical instrument according to claim 2, wherein the fork means is an integral formed portion of the elongated tube.

4. A medical instrument according to claim 1, wherein each jaw element has an inner surface and an outer surface, and wherein inner surfaces of the two jaw elements are adjacent, the second end of each link element being pivotally linked to an inner surface of a respective jaw element.

5. A medical instrument according to claim 4, wherein the first end of each link element is laterally offset relative to the second end by a distance substantially equal to about one half of the thickness of the actuating rod.

6. A medical instrument according to claim 5, wherein the second end of each link element interacts with the linkage end of a jaw element so as to provide stop means for limiting the extent of closing of the jaw means.

7. A medical instrument according to claim 1, wherein the jaw means is a scissor means, and wherein the operative end of each jaw element is a scissor blade.

8. A medical instrument according to claim 1, wherein the jaw means is a grasper means, and wherein the operative end of each jaw element is a grasper arm having a serrated edge.

9. A medical instrument according to claim 1, further including an electrode connected with the elongated tube, and insulating means disposed around the tube and the electrode so as to electrically insulate an exterior surface of the elongated tube from the electrode while providing electrical communication between the electrode and the jaw means.

10. A medical instrument according to claim 9, wherein the electrode is an integral formed portion of the elongated tube.

11. A medical instrument according to claim 1, wherein the two link elements are linked to the actuating rod at opposite sides of the actuating rod through a single pin.

12. A medical instrument according to claim 1, wherein the first end and the second end of each link element are joined by a stepped portion and extend in substantially opposite directions from the stepped portion.

13. A medical instrument, comprising:
    an elongated tube having a first end and a second end;
    jaw means, mounted to the first end of the elongated tube and having two jaw elements pivotally mounted to each other at a pivot point, each jaw element having an operative end and a linkage end, the operative end and the linkage end extending from the pivot point, the operative end and the linkage end of each jaw element being arranged in a substantially coplaner fashion;

an actuating rod for opening and closing the jaw means, the actuating rod having a thickness and being movably disposed within the elongated tube;

linkage means for linking the actuating rod with the jaw means, comprising two link elements, wherein each link element is a substantially planar member lying in a main plane and having a first end lying in a first plane and a second end lying in a second plane, and wherein the first and second planes are substantially parallel to and laterally offset to opposite sides of the main plane of the link element, the first end of each link element being pivotally linked to the actuating rod and the second end being pivotally linked to the linkage end of a respective jaw element; and handle means mounted to the second end of the elongated tube and operably connected to the actuating rod so as to actuate the actuating rod whereby the handle means can be used to actuate the jaw means.

14. A medical instrument, comprising:

an elongated tube having a first end and a second end;

jaw means, mounted to the first end of the elongated tube and having two jaw elements pivotally mounted to each other at a pivot point, each jaw element having an operative end and a linkage end, the operative end and the linkage end extending from the pivot point, the operative end and the linkage end of each jaw element being arranged in a substantially coplaner fashion;

an actuating rod for opening and closing the jaw means, the actuating rod having a thickness and being movably disposed within the elongated tube;

linkage means for linking the actuating rod with the jaw means, comprising two link elements, each link element comprising a body member having a stepped portion and a first end lying in a first plane and a second end lying in a second plane, the first and second ends being joined by and extending in opposite directions from the stepped portion so that the first and second planes of the first and second ends are laterally offset relative to one another, the first end of each link element being pivotally linked to the actuating rod and the second end being pivotally linked to the linkage end of a respective jaw element; and handle means mounted to the second end of the elongated tube and operably connected to the actuating rod so as to actuate the actuating rod whereby the handle means can be used to actuate the jaw means.

15. A medical instrument according to claim 1, wherein each link element is a substantially Z-shaped member wherein the first and second ends correspond to top and bottom arms of the Z-shaped member.

16. A medical instrument according to claim 6, wherein the second end of one link element of the two link elements interacts with the linkage end of a jaw element connected to the second end of the other link element.

* * * * *